US010966680B2

(12) United States Patent
Kagermeier et al.

(10) Patent No.: US 10,966,680 B2
(45) Date of Patent: Apr. 6, 2021

(54) METHOD FOR CONTROLLING THE OPERATION OF A MEDICAL TECHNOLOGY DEVICE, OPERATOR DEVICE, OPERATING SYSTEM AND MEDICAL TECHNOLOGY DEVICE

(71) Applicant: Siemens Healthcare GmbH, Erlangen (DE)

(72) Inventors: Robert Kagermeier, Nuremberg (DE); Gerben Ten Cate, Forchheim (DE); Asa MacWilliams, Fuerstenfeldbruck (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 62 days.

(21) Appl. No.: 16/190,612

(22) Filed: Nov. 14, 2018

(65) Prior Publication Data

US 2019/0150876 A1    May 23, 2019

(30) Foreign Application Priority Data

Nov. 17, 2017    (EP) .................................... 17202205

(51) Int. Cl.
*A61B 6/00* (2006.01)
*A61B 6/10* (2006.01)
(Continued)

(52) U.S. Cl.
CPC ................ *A61B 6/548* (2013.01); *A61B 6/06* (2013.01); *A61B 6/10* (2013.01); *A61B 6/4464* (2013.01);
(Continued)

(58) Field of Classification Search
CPC .. A61B 6/548; A61B 6/10; A61B 6/06; A61B 6/462; A61B 6/4464; A61B 6/467;
(Continued)

(56) References Cited

U.S. PATENT DOCUMENTS

| 2006/0066438 | A1* | 3/2006 | Altounian | ............... G06F 21/86 340/5.53 |
| 2008/0082362 | A1* | 4/2008 | Haider | ................... G16H 70/60 705/2 |

(Continued)

FOREIGN PATENT DOCUMENTS

| DE | 102006046319 A1 | 4/2008 |
| DE | 102008060117 A1 | 6/2010 |

(Continued)

*Primary Examiner* — Michael C Bryant
(74) *Attorney, Agent, or Firm* — Harness, Dickey & Pierce, P.L.C.

(57) ABSTRACT

A method is for controlling operation of a medical technology device using a wireless, hand-held, mobile operator device including a touchscreen. The wireless, hand-held, mobile operator device including a touchscreen is also disclosed. The method includes using the mobile operator device for implementing a medical technology workflow including acquiring patient data of the at least one patient from an acquisition user interface; selecting, via a selection user interface, a medical technology protocol containing operating parameters to be carried out for the at least one patient; setting remote-controllably adjustable components of the medical technology device, according to the at least one patient positioned in the medical technology device and according to the medical technology protocol, using a settings user interface; and activating, with the at least one patient positioned and components set, the medical technology procedure in an activation user interface.

27 Claims, 6 Drawing Sheets

(51) Int. Cl.
*A61B 6/06* (2006.01)
*G16H 30/20* (2018.01)
*G16H 40/63* (2018.01)
*G16H 40/67* (2018.01)
*G06F 3/041* (2006.01)

(52) U.S. Cl.
CPC ............ *A61B 6/462* (2013.01); *G16H 30/20* (2018.01); *G16H 40/63* (2018.01); *G16H 40/67* (2018.01); *A61B 6/467* (2013.01); *G06F 3/041* (2013.01)

(58) Field of Classification Search
CPC ........ G16H 40/67; G16H 30/20; G16H 40/63; G06F 3/041
See application file for complete search history.

(56) References Cited

U.S. PATENT DOCUMENTS

| | | | |
|---|---|---|---|
| 2008/0144777 A1* | 6/2008 | Wilson | A61B 6/542 378/198 |
| 2009/0062937 A1* | 3/2009 | Holstegge | G08C 17/02 700/79 |
| 2016/0242716 A1 | 8/2016 | Dinse et al. | |
| 2018/0206818 A1* | 7/2018 | Dirauf | G06F 1/1626 |

FOREIGN PATENT DOCUMENTS

| | | |
|---|---|---|
| DE | 102013219194 A1 | 3/2015 |
| DE | 102013219195 A1 | 3/2015 |
| DE | 102013219145 A1 | 4/2015 |
| EP | 2034463 A2 | 3/2009 |
| EP | 3352030 A1 | 7/2018 |

\* cited by examiner

METHOD FOR CONTROLLING THE OPERATION OF A MEDICAL TECHNOLOGY DEVICE, OPERATOR DEVICE, OPERATING SYSTEM AND MEDICAL TECHNOLOGY DEVICE

PRIORITY STATEMENT

The present application hereby claims priority under 35 U.S.C. § 119 to European patent application number EP17202205.5 filed Nov. 17, 2017, the entire contents of which are hereby incorporated herein by reference.

FIELD

At least one embodiment of the invention generally relates to a method for controlling the operation of a medical technology device, in particular of an imaging device, wherein a wireless, hand-held, mobile operator device having a touchscreen is used. Further embodiments of the invention generally relate to an operator device, an operating system and a medical technology device.

BACKGROUND

Modern medical technology devices, i.e. in particular larger medical facilities, for examining and/or treating patients are becoming increasingly complex in terms of their features and operation. Consequently, operator control of a medical diagnostic/therapy system represents an implementation challenge in respect of usability and ergonomics. Simple and intuitive operator control is desirable, but often only inadequately implemented in hitherto known medical technology devices. For example, medical examination devices, in particular X-ray devices, are known which have a large number of operator control locations using different operating devices. For example, a display console with keyboard and mouse may be provided in an anteroom adjoining the room in which the medical technology device is disposed, wherein a touchscreen, e.g. on a ceiling-mounted X-ray generator, and/or one or more local operating units (wired or wireless) may additionally be provided as an input device. To control such a medical technology device, the operator therefore often changes operating locations and operating devices, resulting in poor ergonomics.

Solutions proposed in the prior art for simplifying operator control mainly relate to particular operating devices of this kind and their specific implementation to provide specific functions. Thus, for example, DE 10 2013 219 195 A1 proposes a remote control and a method for controlling a device with at least one motion degree of freedom, whereby a movable component of a medical technology device can be controlled on the basis of movements of the remote control, wherein the transmission ratio can be changed for rough positioning and fine positioning. DE 10 2013 219 194 A1 and DE 10 2013 219 145 A1 relate to the use of control elements which can be implemented in particular as joysticks, wherein selection elements are provided for selecting the movable element to be controlled in a medical system, i.e. a medical technology device, or rather a perspective adjustment takes place.

It has recently also been proposed to provide mobile, hand-held operator devices having a touchscreen, in particular commercially available smart devices, for operating medical technology devices. The post-published patent applications DE 10 2017 217 128.6 and EP 17152779.9 relate to different aspects of a portable expansion unit or more specifically one that can be connected to a mobile terminal and into which some safety-relevant functionalities, i.e. functionalities fulfilling safety requirements, can be transferred in order as far as possible to avoid implementing the safety requirements within the commercially available smart device. The expansion unit can be mechanically and/or data-linked linked to the smart device, in particular implemented in the form of an "expansion case".

SUMMARY

At least one embodiment of the invention specifies a simplification, a greater intuitiveness and flexibility and an improvement to the ergonomics for operating a medical technology device.

At least one embodiment of the invention is directed to a method, wherein using an operator device for at least one of an examination and treatment procedure of a patient by the medical technology device, at least the following functions of a medical technology workflow implementing the procedure are implemented via the operator device, comprising:
  acquiring patient data of the patient from an acquisition user interface;
  selecting, via a selection user interface, a medical technology protocol to be carried out for the registered patient and containing operating parameters,
  setting remotely adjustable components of the medical technology device to the patient positioned in the medical technology device and the medical technology protocol to be carried out, using a settings user interface, and
  activating, with the patient positioned and components set, the medical technology procedure in a activation user interface.

At least one embodiment of the invention is directed to a method for controlling the operation of a medical technology device, using a wireless, hand-held, mobile operator device including a touchscreen, the method comprising:
  using the wireless, hand-held, mobile operator device for at least one of an examination and treatment procedure of patient by the medical technology device, the using of the wireless, hand-held, mobile operator device comprising:
    acquiring patient data of the patient from an acquisition user interface,
    selecting, via a selection user interface, a medical technology protocol containing operating parameters to be carried out for the registered patient,
    setting remote-controllably adjustable components of the medical technology device, according to the patient positioned in the medical technology device and according to the medical technology protocol, using a settings user interface, and
  activating, with the patient positioned and components set, the medical technology procedure in an activation user interface.

In addition to the method, at least one embodiment of the invention also relates to a wireless, hand-held, mobile operator device for operating a medical technology device, comprising a touchscreen and a control unit designed to carry out the method according to at least one embodiment of the invention. However, the carrying out of at least one embodiment of the method according to the invention can also be distributed, so that the invention also relates to an operating system for controlling the operation of a medical technology device, the system comprising a wireless, hand-held, mobile operator device having a touchscreen, and a control device comprising a control unit of the operator device and a control unit of the medical technology device and designed to carry out the method according to at least one embodiment of the invention. All statements relating to the method according to at least one embodiment of the invention apply analogously to the operator device and the operating system according to at least one embodiment of the invention, so that the already mentioned advantages can also be achieved therewith.

At least one embodiment of the invention lastly relates to a medical technology device, in particular an imaging device, having an operator device according to at least one embodiment of the invention or rather an operating system according to at least one embodiment of the invention. The previous statements self-evidently also apply analogously to the medical technology device.

At least one embodiment of the invention relates to a wireless, hand-held, mobile operator device for controlling the operation of a medical technology device, comprising:
  a touchscreen; and
  a control unit, designed to, for at least one of an examination and treatment procedure of at least one patient via the medical technology device, carry out a medical technology workflow for at least one of an examination and treatment procedure of the at least one patient via the medical technology device, the medical technology workflow including:
    acquiring patient data of the at least one patient from an acquisition user interface,
    selecting, via a selection user interface, a medical technology protocol containing operating parameters to be carried out for the at least one patient,
    setting remote-controllably adjustable components of the medical technology device, according to the at least one patient positioned in the medical technology device and according to the medical technology protocol, using a settings user interface, and
    activating, with the at least one patient positioned and components set, the medical technology procedure in an activation user interface.

At least one embodiment of the invention relates to a operating system for controlling the operation of a medical technology device, comprising:
  a wireless, hand-held, mobile operator device including a touchscreen; and
  a control device including a control unit of the wireless, hand-held, mobile operator device and a control unit of the medical technology device and designed to, for at least one of an examination and treatment procedure of at least one patient via the medical technology device, carry out a medical technology workflow for at least one of an examination and treatment procedure of the at least one patient via the medical technology device, the medical technology workflow including:
    acquiring patient data of the at least one patient from an acquisition user interface,
    selecting, via a selection user interface, a medical technology protocol containing operating parameters to be carried out for the at least one patient,
    setting remote-controllably adjustable components of the medical technology device, according to the at least one patient positioned in the medical technology device and according to the medical technology protocol, using a settings user interface, and
    activating, with the at least one patient positioned and components set, the medical technology procedure in an activation user interface.

At least one embodiment of the invention relates to a medical technology device, comprising an operating system of at least one embodiment.

At least one embodiment of the invention relates to a medical technology device implemented as an X-ray imaging device, and comprising a radiation protection wall in a room.

BRIEF DESCRIPTION OF THE DRAWINGS

Further advantages and details of the present invention will emerge from the example embodiments described in the following and with reference to the accompanying drawings in which.

DETAILED DESCRIPTION OF THE EXAMPLE EMBODIMENTS

Figure 1:
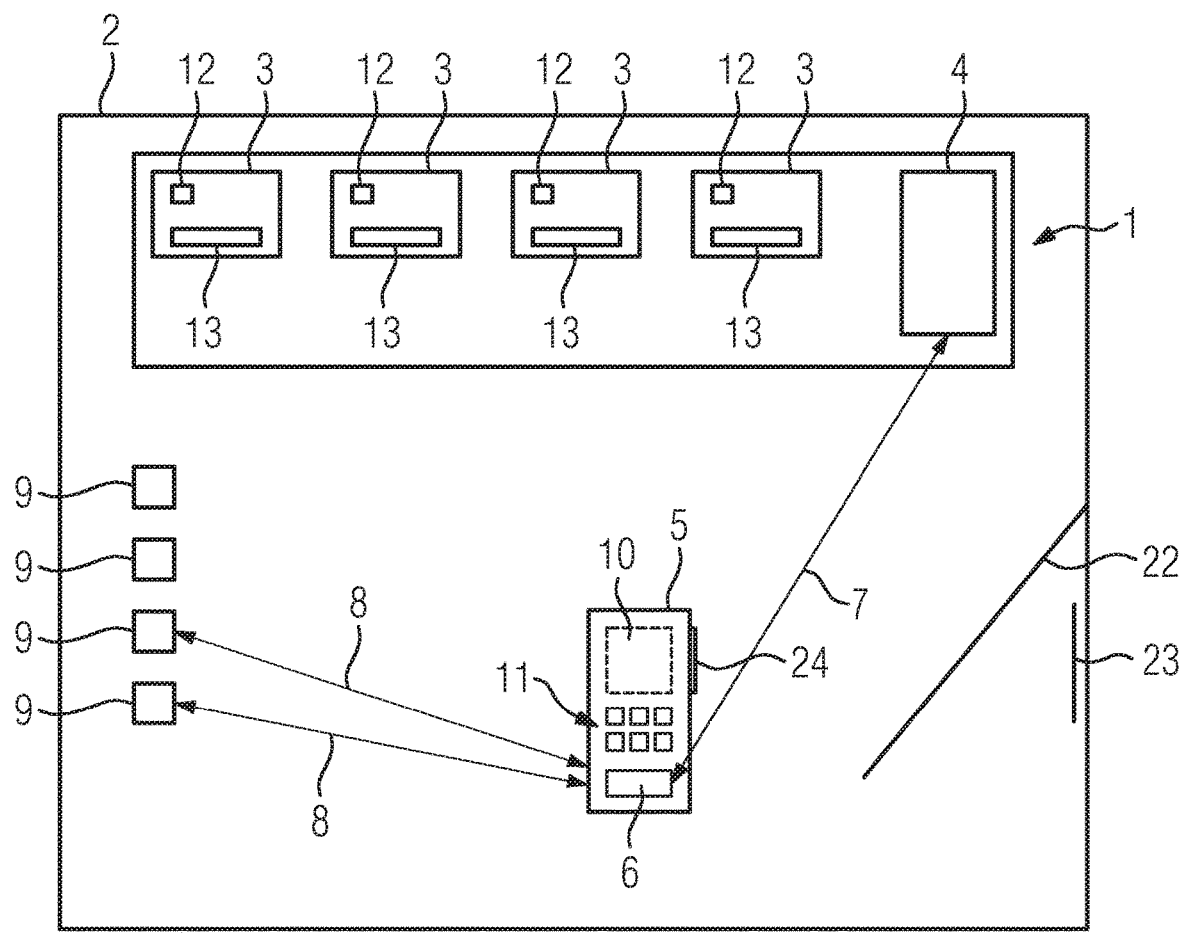
FIG. 1 shows a schematic sketch of components of a medical technology device according to an example embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

At least one embodiment of the invention is directed to a method, wherein using an operator device for at least one of an examination and treatment procedure of a patient by the medical technology device, at least the following functions of a medical technology workflow implementing the procedure are implemented via the operator device, comprising:

acquiring patient data of the patient from an acquisition user interface;

selecting, via a selection user interface, a medical technology protocol to be carried out for the registered patient and containing operating parameters, setting remotely adjustable components of the medical technology device to the patient positioned in the medical technology device and the medical technology protocol to be carried out, using a settings user interface, and activating, with the patient positioned and components set, the medical technology procedure in a activation user interface.

The operator device which is implemented with particular preference as a smart device, thus in particular a smartphone and/or tablet of the commercially available kind, consequently has a touchscreen on which various user interfaces assigned to different steps/functions of the medical technology workflow which implements the patient's examination and/or treatment procedure can be displayed and offer corresponding input options.

For this purpose the operator device has in particular a control unit on which a control computer program is at least partially executed, in particular as an app. The operator device preferably also has at least one radio interface, so that it is designed for wireless communication with a control unit of the medical technology device, wherein the control unit of the operator device and the control unit of the medical technology device can interoperate as a control device in order to implement different aspects of the method according to an embodiment of the invention, as will be examined in greater detail below. In particular, the communication link between the control unit of the medical technology device and the control unit of the operator device allows, on the one hand, control information generated from user inputs to be transmitted via corresponding radio interfaces to the control unit of the medical technology device in order to implement it accordingly, and/or, on the other hand, allows feedback information and/or status information from the control unit of the medical technology device to be provided to the control unit of the operator device in order to display the information accordingly and/or to operate the operator device. The information can be displayed accordingly via the user interfaces. Additional information links e.g. to an information system (RIS/HIS) can self-evidently also be present.

Using a powerful, portable, small-format touch display unit, in particular a smart device, as an operator device consequently makes it possible to implement the complete medical technology workflow on a single operator device, thus achieving ergonomic, simple, intuitive and complete user control of a medical technology device, and hence of a medical facility. The medical technology device may be designed in particular as an X-ray imaging device, so that by way of example the complete medical technology workflow of an X-ray examination can be implemented therewith. In general terms, full operator control of the medical technology device is possible directly from the operator's hand via an appropriate smart design of the different user interfaces on the touchscreen and there is no longer any need to frequently change the operating location and/or the operating device. For an operating concept of this kind, an embodiment of the present invention even obviates the need for an anteroom for controlling the medical technology device, wherein in the case of an X-ray device it can be provided that a radiation protection wall is disposed in the examination room.

In short, in an embodiment, it is therefore proposed to replicate the operator control functions and sequences on a portable, wireless, mobile operator device allowing complete, simple and intuitive operator control of a medical technology device, in particular of an imaging device, in an operator-oriented manner. It is therefore no longer necessary to change operating locations. All the functions of the medical technology workflow as well as information arising and/or used are available in an operator- and patient-oriented manner.

The operator therefore carries the operator device with him/her throughout the examination and/or treatment procedure and can thus, for example, acquire the patient data directly from the patient in a waiting room. After acquisition of the patient to be examined, the possible examination and/or treatment protocols, i.e. medical technology protocols, can be clearly displayed visually on the operator device. The operator device is likewise used for setting up and positioning the patient and/or the medical technology device. Finally, when patient positioning and correct setting of the medical technology device are complete, execution of the selected medical technology protocol can be initiated.

In a specific embodiment it can be provided that at least some of the patient data is ascertained by readout of an electronically readable code, in particular a barcode and/or a QR code, via a camera of the operator device, and/or by reading a radio readable code, in particular an RFID tag and/or an NFC tag, via a radio readout interface of the operator device. It is therefore conceivable within the scope of the present invention to use both an optical sensor, in particular a camera, and an integrated radio readout interface, in particular RFID or NFC, for reading in the patient data. The data can be read in from an information medium which can be implemented e.g. as a patient wristband. Other information media such as NFC tags and/or RFID tags, for example, can obviously also be used. The patient data can be read in directly from the patient thanks to the mobile operator device. Readout of the information medium can be initiated via a corresponding operator control element of the acquisition user interface. In addition or alternatively to machine-based readout of the patient's information medium, the acquisition user interface can self-evidently also permit operator entry of patient data.

Read-out patient data can preferably be displayed on the touchscreen for checking and/or modification by the operator. This enables the operator to verify directly, in particular from a patient management user interface, not only after readout but also after changing of the active patient, that this is the correct patient. This is important particularly when patients are collected in turn from a waiting room for their examination. For example, the patient's name, date of birth and/or age can be displayed as patient data. The patient can be asked for the patient data displayed in order to confirm his/her identity. Particularly when changing back to that patient registered at an earlier time, the corresponding sub-user interface of the acquisition user interface can include a Confirm control element which confirms that the correct patient has been collected from the waiting room.

When there are a plurality of patients to be examined, the operator device can expediently have, outside of the medical technology workflow for a current patient, a patient management user interface via which, in particular by use of a list of patients, the patient sequence is adjusted according to a user input and/or switching to the medical technology workflow of another patient takes place according to the user input. Therefore, if there are a plurality of patients to be examined and/or treated, the operator device can provide access to the list of patients in order to make a change to the patient sequence irrespective of the position of the operator, in particular in the waiting room itself. This can take place, for example, if a patient requires examination more urgently. This greatly simplifies existing operating systems where this has only been possible on a display console in an anteroom. For example, the patient management user interface can be called up from each of the workflow-related user interfaces via a corresponding operator control element and/or a corresponding operator gesture on the touchscreen.

The patient management user interface also allows switching to another patient, in particular after a previous patient has been registered and/or a medical technology workflow for a previous patient has been completed. In practice it is often the case that a patient is registered first, e.g. in a waiting room, and possibly at least one medical technology protocol is even already selected in the selection user interface. However, other patients are examined/treated before this registered patient in the sequence, so that the patient whose turn it is, is temporarily reverted to and the medical technology workflow of the registered patient is not continued until later.

In an advantageous development of the method according to an embodiment of the invention, it can be provided that, in the case of a foreign-language patient, foreign-language information relating to the current position in the medical technology workflow is output to the patient and/or words of the patient recorded using a microphone of the operator device are translated into a language of the operator and output. For audio output, the operator device can expediently have an integrated loudspeaker. This can facilitate communication with foreign-language patients. On the one hand it is conceivable to provide audio output of predefined speech sequences which can preferably be output in a triggered manner. They can be triggered, for example, as a system event when a particular position in the medical technology workflow is reached and/or when particular feedback information is input, but they can also be initiated by a user input.

It is additionally or alternatively possible for patient utterances to be translated in real time via a suitable translation program and reproduced, wherein they can conceivably be output here both via a loudspeaker and in text form. Translation can take place automatically whenever a corresponding translation function has been activated. Appropriate translation program, which can possibly be adapted to the patient via test sentences, have already been proposed in the prior art. The appropriate language for the communication aids can preferably be selected during acquisition of the patient data in the acquisition user interface. The corresponding functions can also be activated there.

In a preferred development it can be provided that, together with the patient data, medical information describing the examination and/or treatment objective is determined, in accordance with which medical technology protocols and/or the sequence thereof and/or a medical technology protocol proposal are selected in the selection user interface.

Whereas an objective of using the medical technology device, e.g. the region of interest and/or the diagnosis to be made in the case of an imaging device, can be derived from a user input, in particular in the acquisition user interface, it is self-evidently also conceivable to retrieve this information from a database and/or an information system with which a communication link exists from the operator device and/or the control unit of the medical technology device. For example, the medical information can be retrieved from an electronic patient file and/or a hospital information system (HIS) and/or a radiology information system (RIS). Depending on the medical information, possible medical technology protocols, e.g. examination protocols such as imaging protocols, can be assessed for suitability and it is possible to select which medical technology protocols are to be displayed in the selection user interface and in what sequence. Expediently a specific medical technology protocol proposal is even made in the form of a recommendation in respect of the medical information. This further simplifies the operating process by automatic evaluation of available medical information.

It is especially advantageous particularly when using a commercially available smart device as an operator device if, for safety-relevant control commands of the operator, in addition to the operator device an expansion unit is used which can be linked to the operator device mechanically and/or for data transmission. The expansion unit can have at least one operator control element, in particular an enabling switch, for approving a safety-relevant control command. It allows the safety-relevant component to be transferred away from the operator device which does not therefore need to fulfill all the safety requirements. The expansion unit is preferably connected to the operator device both mechanically, e.g. as an expansion case, and via a data transmission link, as described in particular in the post-published patent applications DE 10 2017 217 128.6 and EP 17152779.9 already mentioned in the introduction, the entire contents of each of which are hereby incorporated herein by reference. For example, safety-related inclusion of an enabling switch for moving components of the medical technology device and/or initiating the automatically executed medical technology protocol can be provided.

In a specific embodiment of the expansion unit which is designed to control safety-relevant functions of the medical technology device, the unit can include:
- a holder that can be matched to the size of the flat-format, portable operator device and which is designed to detachably connect the expansion unit mechanically to the portable operator device, and
- a first communication module which is designed to establish a safety-oriented data connection to the medical technology device and/or the operator device.

The holder can be designed, for example, to clip the expansion unit to the portable operator device from the underside of the operator device so that a kind of "expansion case" is provided. As an operator control element, the expansion unit can have a switch on the holder which is designed to be actuated by a user of the expansion unit using the hand holding the expansion unit.

It can additionally and/or alternatively also specifically be provided that the expansion unit for the mobile operator device comprises:
- a power supply via the operator device,
- a preferably wireless data interface for the transmission of safety-relevant data by the operator device,
- a processor unit designed to process safety-relevant data, and
- a number of operator control elements for entering safety-relevant data.

The power supply and the data interface can be implemented as a common interface, in particular an NFC interface.

Such an expansion unit is used in particular, as already mentioned, if control commands for moving at least one component of the medical technology device and/or for initiating the actual examination and/or treatment procedure in accordance with the medical technology protocol are to be generated as control information. Thus, for example, via the safety-oriented inclusion of an operator control element of the expansion unit, in particular an enabling switch, in addition to acquiring user inputs on the touchscreen, safe movement of components of the medical technology device can be executed.

It is generally expedient, as will be explained in greater detail below, to record and possibly also track the position of the operator device at least at times, in particular continuously, in the form of position data, wherein at least one function and/or at least one user interface of the medical technology workflow can be adjusted in accordance with the position data. If the operator device is implemented as a smart device it is particularly preferred if the operator device sensors usually already provided there anyway are used. For example, the operator device implemented in particular as a smart device can have at least one operator device sensor acquiring sensor data describing the movement and/or the position of the operator device at least in the room in which the medical technology device is located, wherein the position data describing the position and orientation of the operator device and/or movement data describing a movement of the operator device is determined from the sensor data and taken into account for the implementation of at least one function of the medical technology workflow.

A specific embodiment in this context provides that the operator device implemented in particular as a smart device has at least one operator device sensor acquiring sensor data describing the movement and/or the position of the operator device in the room in which the medical technology device is located, wherein position data describing the position and the orientation of the operator device with respect to the components to be adjusted and/or movement data describing a movement relative to the components is determined from the sensor data and evaluated for selecting at least one of the components and/or for ascertaining an operator input in respect of at least one of the components. This provides particularly intuitive and patient-oriented operator control of component movements for medical technology devices, wherein it is particularly advantageous if the sensor system already present in the smart device is used, in order to allow complete location and position detection (and therefore also motion detection) of the smart device in the room in which the medical technology device is located.

The medical technology device has a device of determining current setting information of components which describes the position thereof in the room, as is essentially known, which means that, e.g. in the control unit of the medical technology device, the system geometry can be as precisely known as the current setting of the actuators for moving/adjusting the components, the setting being determinable e.g. by motor encoders or corresponding sensors. Since the position of the medical technology device in the room is also known, the relative positions and orientations and/or movements of the at least one component and of the smart device can be determined and evaluated in respect of remote control of the components.

It is therefore possible in particular to point intuitively at components and/or make corresponding movements with the smart device for remote control of components, thus allowing operation in a convenient manner and in sight of the components to be controlled. For this purpose the operator device is preferably oblong, i.e. in particular essentially rectangular and flat in shape, so that the operator device can be aimed at the components to be operated.

If a camera is used as the operator device sensor, optical markers disposed in the room whose position in the room is known can be detected in the image data thereof and used to determine the position data and/or the movement data. Also conceivable are active markers to which a short-range radio connection can be established. The possibility of establishing such a short-range radio link, in particular via Bluetooth/Bluetooth Low Energy, or rather the characteristics thereof can be evaluated in order to check the proximity of the operator to the components to be adjusted and, for example, to activate the corresponding settings user interface accordingly. Sensors other than cameras can self-evidently also be used as operator device sensors, e.g. accelerometers and/or angular rate sensors for implementing dead reckoning, in particular in addition to marker navigation, e.g. if the latter fails and/or plausibility checking is required.

Although the component to be operated can be selected via the touchscreen, to select a component to be controlled it is preferable in this context to evaluate the operator device orientation contained in the position data to ascertain whether the operator is pointing the operator device at one of the at least one components, which, in particular after actuation of a Confirm control element by the operator, is selected. In this embodiment the operator therefore points the smart device at the component to be operated in order to select it and relate subsequent operator inputs to that component. For example, the smart device's longitudinal axis known from the position data can be extended and checked as to which component it (initially) relates to. This allows particularly intuitive selection. The selection can be displayed on the touchscreen, but preferably by the component itself, in particular via an output device which can be implemented as an LED strip and/or a backlightable color surface. This prevents an unpleasant change of focus.

The movement that is to be performed by the selected component can take place either by actuating appropriately labeled touch control elements or preferably by gestures with the operator device which are described by the movement data (e.g. movement of the operator device laterally and/or vertically, rotation of the operator device in an axis and similar). These gestures or rather movement data are then translated into motion degrees of freedom of the selected component, e.g. of a patient table and/or of a detector. By use of the location and position information of the operator device, i.e. the position data, always correct left/right, forward/back motion viewed from the operator's standpoint can be activated intuitively. Specifically it can therefore be provided that the movement of a component selected as operator input from the one or more components on the basis of movement data takes place according to the movement of the operator device, in particular the position and orientation of the operator device with respect to the component.

In this context it should also be pointed out that, since movements in the patient environment may be considered safety-critical, the already mentioned expansion unit can be used at least for some of the components, so that, for example, an operator control element, in particular an enabling switch, of the expansion unit must be actuated to initiate and/or track the movement described by the movement data.

Moreover, it can also be generally be expedient if at least one movement of the operator device is detected and evaluated to determine a gesture as operator input. In this way, not only inputs via the touchscreen and/or other operator control elements of the smart device can be used, but operation by gesture is also possible, wherein accelerometers and/or angular rate sensors and/or magnetometers in particular can be used as operator device sensors for acquiring the corresponding movement data.

In an extremely specific embodiment in respect of the adjustment of components, a preferred development provides that, to operate a collimator as a component of a medical X-ray imaging device as a medical technology device which comprises an X-ray generator to which the collimator is assigned, an X-ray detector, and a patient table for positioning the patient to be X-rayed, a display visualizing the current setting of the collimator is generated on the touchscreen and the collimator is adjusted according to operating data describing a manipulation of display elements of the display, wherein position information describing the position and/or orientation of the operator is determined from sensor data of at least one sensor and is used to select a perspective corresponding at least approximately to the operator's angle of view of the patient table for the three-dimensionally visualizing display showing the radiation beam with the current collimator settings. Using determined location and position information of the operator device (and therefore of the user carrying it), a three-dimensional representation of the X-ray beam in correlation with the actual X-ray device can be displayed, so that the amount of beam limiting by the collimator can be controlled e.g. via corresponding simple gestures. Alternatively to an embodiment of this kind, the collimator setting can also be controlled via other sub-user interfaces, e.g. a two-dimensional representation of the collimator setting and similar.

It should also be noted at this juncture that, in particular also on the basis of the medical information, a plurality of medical technology protocols can be selected as "to be carried out", wherein a sequence is then expediently likewise defined. The steps of the medical technology workflow can then be repeated for each of these individual medical technology protocols after selection.

A selected medical technology protocol may already be assigned suitable basic settings of settable components which can be selectable accordingly in the settings user interface, wherein after selection by the operator the basic settings are made automatically. Fine adjustments can then be made or the settings can be accepted unchanged. Independently of a selected medical technology protocol, different basic settings, e.g. marked graphically in an abstract representation of the human body, can also be offered in a sub-user interface at the start of setting.

In the selection user interface or else, if the sequence of a plurality of medical technology protocols has not been defined, when moving to the settings user interface, medical technology protocols can also be graphically visualized e.g. by marking of corresponding body locations to be examined and/or treated in an in particular abstract representation of a human body.

As regards initiating execution of a selected medical technology protocol, it is again expedient, particularly in the case of somewhat safety-critical procedures such as irradiation of the patient, to use the described expansion unit, e.g. actuate there an appropriate operator control element, in particular an enabling switch.

If a user input indicates initiation of the examination and/or treatment procedure, i.e. specifically of the selected medical technology protocol, particularly in the case of a medical technology device using radiation, in particular an X-ray imaging device, the position of the operator device can be determined and checked as to whether the operator device and therefore the operator are in a radiation-shielded location, wherein triggering is enabled and/or takes place only if the check is successful. When patient positioning is complete and/or the components have been set, the operator device can therefore also be used to release radiation in the case of a radiation-using medical technology device, wherein the safety-oriented use of the expansion unit is available. By use of available position data of the operator device, radiation triggering can also only be enabled if the operator stays behind a radiation protection wall or at another radiation-shielded location, in particular outside the room in which the medical technology device is located. For example, an Operate control element can be grayed out if the operator is in an unsafe location, and/or a warning can be issued to the operator.

In a particularly preferred embodiment of the present invention it can be provided that, as an additional function of the medical technology workflow for an examination procedure, a first output of the examination result, in particular of an acquired image, is provided in an assessment user interface. In the case of an imaging device as the medical technology device, the acquired image can therefore be assessed immediately on the operator device, wherein a zoom functionality and/or a high-resolution, high-quality touchscreen also on the small-format operator device allow a sufficiently good assessment. In particular, it can also generally be provided that the touchscreen has a 5 to 6 inch display diagonal and/or is high-resolution. Using an assessment user interface enables another expedient workflow step of the medical technology workflow to be added and implemented via the operator device.

In this context it is particularly advantageous, in the case of an image as the examination result, if the assessment user interface provides at least one image processing option, on the selection of which an image processing algorithm corresponding to the image processing option is applied to the image, and/or a zoom function and/or an annotation function. A recorded image can therefore not only be processed, but also post-processed if required, e.g. by cropping, adjusting the brightness and/or contrast and the like. It is also advantageously possible for the image to be provided with comments, in particular therefore by annotation, wherein voice input via the already mentioned microphone can expediently be used for annotations.

It is also particularly expedient if the assessment user interface comprises a Finish control element which, when actuated, causes the medical technology result to be transmitted to an archiving system. On completion of the medical technology workflow, the medical technology workflow of the next patient in line can be accessed and/or the operator can switch to the patient management user interface.

Also in this context, the expansion unit can again be expediently employed if the examination process is to be more safely flagged as completed. On completion of the examination process, a final assessment can take place directly on the operator device and, if the examination result is of sufficient quality, the medical technology workflow can be terminated with archiving of the examination result, e.g. on an information system (HIS/RIS). Thus complete execution of the medical technology workflow including a provisional assessment of the examination result can be implemented in an intuitive and simple manner using the mobile operator device as the single control device.

In the case of a plurality of examinations on the same patient, the steps of the medical technology workflow can be repeated with the exception of the acquisition of the patient data. If in the case of an imaging device, for example, a plurality of images are therefore to be taken on the same patient, this is made easily possible by repetition of the to-be-repeated steps of the medical technology workflow for the different medical technology protocols.

It is also expedient if switching between the different user interfaces of the medical technology workflow is effected in response to a switch gesture on the touchscreen, in particular a swiping gesture. This allows easy navigation between the individual workflow steps on the touchscreen. Simple horizontal swiping gestures are preferably used, wherein forward/back control elements and/or tabs can alternatively and/or additionally be used.

In addition to the method, at least one embodiment of the invention also relates to a wireless, hand-held, mobile operator device for operating a medical technology device, comprising a touchscreen and a control unit designed to carry out the method according to at least one embodiment of the invention. However, the carrying out of at least one embodiment of the method according to the invention can also be distributed, so that the invention also relates to an operating system for controlling the operation of a medical technology device, the system comprising a wireless, hand-held, mobile operator device having a touchscreen, and a control device comprising a control unit of the operator device and a control unit of the medical technology device and designed to carry out the method according to at least one embodiment of the invention. All statements relating to the method according to at least one embodiment of the invention apply analogously to the operator device and the operating system according to at least one embodiment of the invention, so that the already mentioned advantages can also be achieved therewith.

In particular, to implement the method according to at least one embodiment of the invention a control computer program is therefore used which is executed at least in part to generate the different user interfaces in the control unit of the operator device. Other component parts of at least one embodiment of the inventive method, e.g. determining position data and/or movement data or rather the specific determination of control information can also be carried out on the control unit of the medical technology device itself which is usually provided in a main unit, e.g. a gantry of a CT scanner as the medical technology device, a C-arm stand and the like.

In an advantageous development of the operator device according to at least one embodiment of the invention or rather of the operating system according to the invention it can be provided that the operator device has at least one carrying device for attachment to the operator, in particular a belt clip and/or a carry strap. In order to be able to store the portable operator device quickly and easily when it is not being used, a belt clip, for example, can be mounted on the back in order to enable it to be hung from the belt or a pocket. Also conceivable is a carry strap on which the operator device is hung.

At least one embodiment of the invention lastly relates to a medical technology device, in particular an imaging device, having an operator device according to at least one embodiment of the invention or rather an operating system according to at least one embodiment of the invention. The previous statements self-evidently also apply analogously to the medical technology device.

The medical technology device can in particular be implemented as an X-ray imaging device which, in a room in which it is disposed, comprises a radiation protection wall. Particularly if, because of the operating concept presented, an anteroom for controlling the medical technology device is dispensed with, it is expedient in the case of radiation-using medical technology devices, in particular X-ray devices, to use a radiation protection wall in the actual examination room.

Disposed behind this radiation protection wall, but also independent of any such radiation protection wall, the medical technology device can also have with particular advantage, as an additional operator device, a touchscreen of larger diameter than the touchscreen of the operator device, this being particularly useful in order to be able to provide a larger image as an examination result and a better assessment via the assessment user interface. If the medical technology device is an X-ray imaging device, a larger monitor, in particular likewise implemented as a touchscreen, can therefore be mounted behind the radiation protection wall in order to enable acquired X-ray images to be viewed and assessed directly in a larger format, possibly in particular to initiate another image capture.

FIG. 1 shows a schematic sketch of an example embodiment of the inventive medical technology device 1 which is disposed in a room 2 and is implemented here as an X-ray device. The medical technology device 1 has a plurality of adjustable components 3 which can be moved e.g. by remote control. The components 3 can include, for example, an X-ray generator, an X-ray detector, a collimator and a patient table. The operation of the medical technology device 2 is controlled by a control unit 4.

Provided as the operator control device of the medical technology device 1 is a wireless, hand-held and mobile operator device 5 implemented here as a smart device, specifically a smartphone, the control unit 6 of which can establish a wireless communication link 7 to the control unit 4 via a corresponding radio interface (not shown in greater detail here), in particular a Bluetooth interface and/or preferably a WLAN interface. The Bluetooth interface, wherein Bluetooth Low Energy (BLE) is used here, is otherwise also used to set up short-range radio links 8 to at least some optical markers 9, specifically at least to active optical markers 9 which can therefore be activated to output optical signals to be detected.

It should be already be pointed out at this juncture that the option for establishing short-range radio links 8 or rather the characteristics thereof can also be used as a general trigger which indicates that the operator device 5 is in the room 2 or at least close to the components 3, so that adjustments to the components 3 can be made via the operator device 5 in the medical technology workflow for the examination of a patient. In particular, more precise position determination of the operator device 5 can be initiated which will be described in greater detail below. The operator device 5 also comprises, as is generally known, a touchscreen 10 as an operating device and display. The operator device 5 also has operator device sensors 11, here two cameras, namely a front camera and a rear camera, accelerometers, angular rate sensors and a magnetometer which acts as a compass.

To provide the adjustability, the settable components 3 are assigned actuators 12, e.g. motors, controllable by the control unit 4 which also report their respective setting to the control unit 4 so that the latter, because of the likewise thereto known system geometry of the medical technology device 1, constantly knows the settings, in particular the positions, of the components 3. The control unit 4 also knows the position of the medical technology device 1 in the room 2. This makes it possible, in particular, for a known position and orientation or known movement of the operator device 5 in the room 2 as corresponding position data and movement data respectively, to place the latter in relation to the components 3 so that adjustments can be made to these components 3 via the operator device 5, as will be explained in greater detail. In particular, a component 3 to be adjusted can be selected via the operator device 5 and a required setting can be entered via the operator device 5 by the movement thereof.

In respect of the selection of a component 3 to be set, the components 3 have output devices 13, e.g. LED strips, the illumination of which clearly indicates that the corresponding component 3 has been selected for operation. Thus an indication can be provided without an operator having to look away from the component 3.

Position data and/or movement data of the operator device 5 in the room 2 and also outside the room 2 can be used in a variety of ways within the scope of the present invention, i.e. in particular during a medical device workflow for carrying out a patient's examination procedure. To determine the position data and movement data, and therefore the orientation, position and also movement of the operator device 5, the markers 9 in the room 2 are used which can be detected via the cameras. This will be explained in greater detail with reference to FIG. 2.

Figure 2:
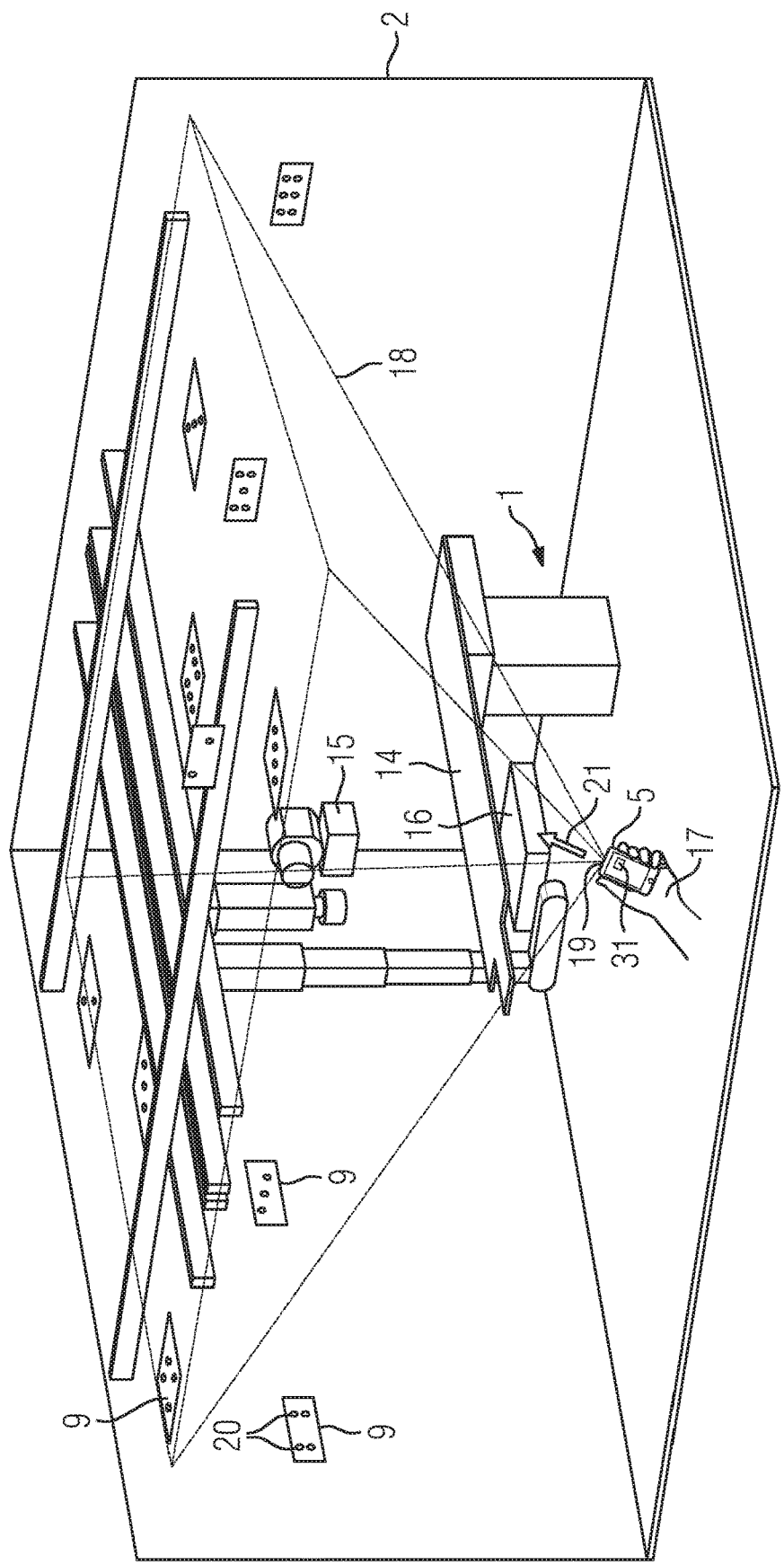
FIG. 2 shows a representation for explaining localization by way of markers and a camera of an operator device.

FIG. 2 shows a perspective view of the room 2. It firstly shows the medical technology device 1 comprising the patient table 14, the X-ray generator 15 and the X-ray detector 16 as components 3. The collimator (not shown in greater detail here for the sake of clarity) is an integral part of the X-ray generator 15. An operator's hand 17 holds the operator device 5 in the room 2, wherein the coverage area 18 of the front camera 19 as an operator device sensor 11 is indicated. The markers 9 clearly distinguishable in their visually perceptible pattern can be seen at different locations in the room 2, here for the sake of clarity distributed at least over the ceiling and walls; it is obviously also possible for optical markers 9 to be disposed on the floor. The active markers 9 here have infrared LEDs 20 in different patterns.

Since the operator device 5 is flat and oblong, it also has, when lying in the hand 17, a clearly defined pointing direction 21, symbolized by an arrow, namely the extension of the longitudinal axis of the operator device 5.

At least when the operator device 5 is in the room 2 the markers 9 are used to determine highly accurate position data and movement data of the operator device 5, this happening continuously in the control unit 4 and/or the control unit 6. If the markers 9 are insufficiently detectable, e.g. because the operator device 5 is outside the room 2, position data and/or movement data can still be determined via external sensors, other markers, radio-based position determinations and the like, wherein movement data can be additionally and/or exclusively determined from accelerometer and/or angular rate sensor data.

Since the position and characteristics of the markers 9 have been determined in a configuration phase, these are now stored and available e.g. in a database. The markers 9 detected by the camera 19 can therefore be used for position determination, wherein the active markers 9 can be activated by the short-range radio links 8 to output corresponding, detectable signals in synchronization with the operator device 5. The infrared LEDs 20 enable the markers 9 to be reliably detected. Because of the short-range radio link 8, the active markers 9 also act as radio beacons or light signals, which already allows at least rough position determination (delay and field strength measurements). Such rough position determination could also be achieved using actively light-transmitting optical markers acting as light beacons by modulation of an identification signal. To support the sensor data of the camera, the sensor data of the accelerometers (tilting in the room), of the angular rate sensors (motion) and of the magnetometers (orientation to the north roughly determinable) is also taken into account.

Figure 3:
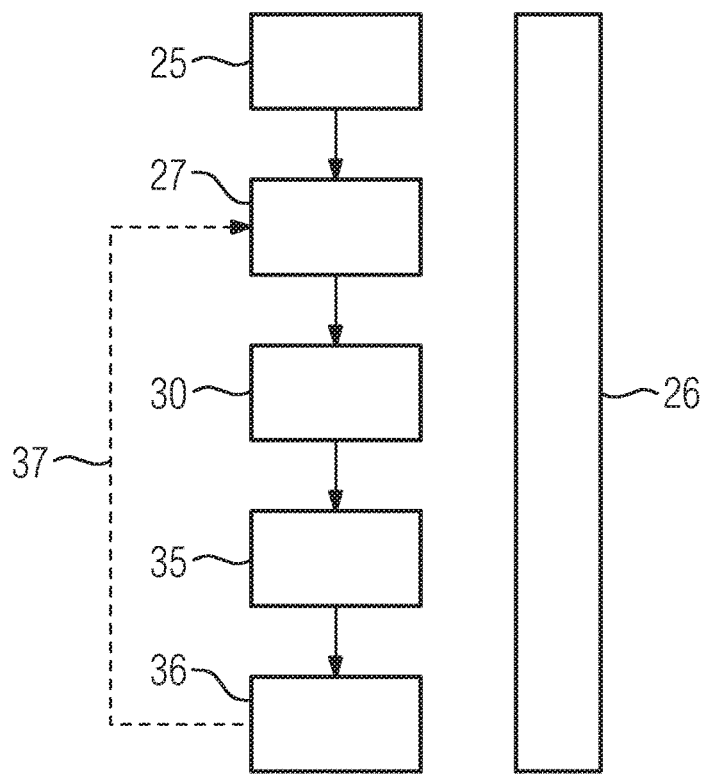
FIG. 3 shows a flowchart of a medical technology workflow with the medical technology device.

FIG. 3 now explains different steps of a medical technology workflow for examining a patient, wherein all the operator control functions during the medical technology workflow can be implemented using solely the operator device 5, thereby providing an integrated operating concept without changing of operating locations or operating devices. In this context, an embodiment of the present invention obviates the need for an anteroom with an operator console, for which reason, cf. FIG. 1, there is also provided in the room 2 a radiation protection wall 22 behind which a display device 23, here likewise implemented as a touchscreen, is also provided for larger display of acquired X-ray images as examination results, the display device having a larger display area than the touchscreen 10. It should also be pointed out at this point that, for times when it is not in use, the operator device 5 can have a carrying device 24, e.g. belt clip and/or a carry strap.

If a patient is now to be examined, specifically an X-ray image of the patient is to be taken, the corresponding medical technology workflow implementing this procedure for that patient begins with a registration step 25 in which patient data of the patient is acquired, i.e. the patient is registered. For this purpose there is displayed on the touchscreen 10 of the operator device 5 an acquisition user interface in which patient data can be entered manually or else a readout process can be initiated whereby a camera 19 of the operator device 5 and/or a radio readout interface (not shown), in particular an RFID interface and/or an NFC interface, is used to read an information medium, e.g. a patient wristband. Patient data read from the information medium is displayed in the acquisition user interface for checking/verification/modification, wherein a corresponding display also re-appears when switching to a new, already registered patient. Patient data can also be retrieved, at least partially and in particular after identification of the patient by reading of the information medium, from an information system or more specifically from a database, in particular a hospital information system, a radiology information system and/or an electronic patient file, in particular medical information describing the examination objective of the examination process.

For acquisition of the patient data, there can also be activated, via corresponding control elements of the acquisition user interface, a foreign-language functionality which allows not only audio output to the patient of foreign-language information relating to the current position in the medical technology workflow via a loudspeaker of the operator device 5, but also activates a translation program for automatically translating patient speech recorded by a microphone of the operator device 5 and outputting it in text form or via the loudspeaker.

Even at this point it should be noted that parallel management of patients is also possible, wherein a patient management user interface superordinate to the workflow user interfaces, reachable from the workflow-related user interfaces via a corresponding operator device, is denoted by the box 26. There a list of patients is displayed for which the patient sequence can also be changed, e.g. in the event of an emergency arrival. In particular, the patient management user interface also allows switching between patients, since patients are often registered much earlier (and a medical technology protocol, here examination protocol, is selected) than when it is their turn for the actual examination.

Figure 4:
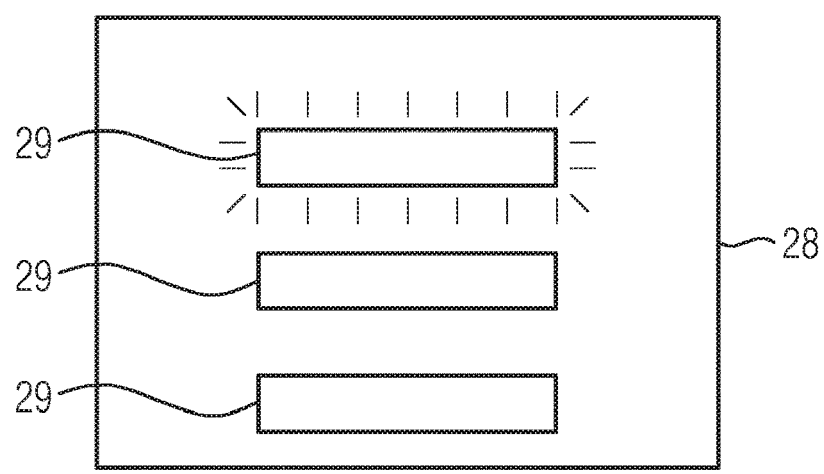
FIG. 4 shows a schematic sketch of a selection user interface.

Once the patient data of a patient has been acquired, the next step in the medical technology workflow (here examination workflow) for that patient is step 27 for selecting the at least one examination protocol to be carried out (generally medical technology protocol). Examination protocols are well known in the prior art and contain operating parameters of the medical technology device 1 with which X-ray images that are suitable for corresponding assessment are achieved as the examination result. Since background knowledge is already available on the basis of the medical information that has been acquired with the patient data, a preliminary selection of possible examination protocols and even a recommendation can be output. A corresponding selection user interface 28 is schematically illustrated in FIG. 4. There an intuitively usable list of examination protocols 29 is output on the touchscreen 10 whose sequence and recommended selection (highlighted examination protocol 29 in FIG. 4) is determined on the basis of the medical information. Graphical selection using an abstractly displayed human body and corresponding examination areas is also possible.

After selection of the examination protocol in step 27, the patient in the room 2 is positioned on the patient table of the medical technology device 1 and the components 3 are set to the examination protocol 29 to be carried out and the patient. This occurs in step 30 which can take place via a settings user interface which possibly has sub-user interfaces for different components 3. Another sub-user interface can be used to select basic settings of a general kind and/or for the selected examination protocol 29 and/or to confirm the setting thereof for assignment to a selected examination protocol 29 and/or, if a plurality of examination protocols 29 are selected whose sequence has not been specified, to select a now to be carried out protocol (and therefore possibly corresponding basic settings). After selection/confirmation, the basic settings can be automatically implemented.

Figure 5:
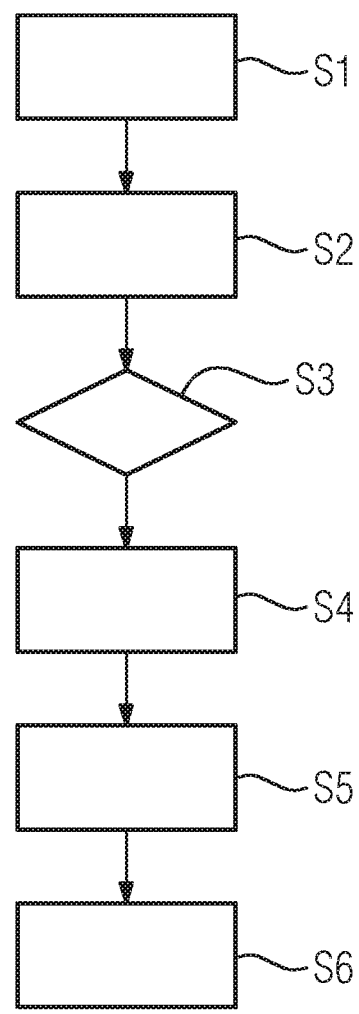
FIG. 5 shows a flowchart for setting a component as part of the method according to an example embodiment of the invention.

For movable components, a particularly advantageous operating variant can be implemented which will be explained in greater detail below with reference to the flowchart in FIG. 5.

In a step S1, the user aims the operator device 5 at the component 3 to be controlled. The continuation of the longitudinal axis, i.e. the pointing direction 21, can be determined from the current position data so that it can be checked whether the operator device 5 is pointing at a component 3. If this is the case, in a step S2 the output device 13 assigned to this component is placed in a selectability mode, e.g. for emitting a first color. It is then determined in a step S3 that a confirmation operator control device, in this case displayed on the touchscreen 10, has been actuated, in a step S4 the corresponding component is finally selected as "to be operated" and the output light of the output device 13 changes color, e.g. from yellow to green, by way of confirmation.

In a step S5 it is now possible, via another operator control device likewise displayed on the touchscreen, here a movement enabling button 31 (cf. FIG. 2), to translate movements of the operator device 5 into movements of the component 3 selected. For example, if in FIG. 2 the X-ray generator 15 is selected and if the operator device 5 is moved to the right, the X-ray generator 15 also moves to the right as long as the movement enabling button 31 is actuated. The same applies to rotations or other movements, provided these motion degrees of freedom are available.

A step S6 symbolizes another possibility for remote control of a component 3, namely selection of a target position by the operator device 5 by pointing at it and actuating a target selection operator control device which can again be displayed on the touchscreen 10. The component 3 is then moved to the corresponding target position.

In addition, a de-selection operator control device or rather a re-selection operator control device can also be provided in order to mark other components 3 for control. Self-evidently, components 3 may also be linked to one another, which applies e.g. to the X-ray detector 16 and the X-ray generator 15 at least in respect of some motion degrees of freedom. All this is implemented in the control unit 4.

Further settings of adjustable components 3, apart from movements, can also be made in step 30 via the settings user interface and its sub-user interfaces. Another example, that of a collimator, will be explained with reference to FIG. 6.

It should be noted beforehand that the collimator of the medical technology device 1 has adjustable beam limiting elements in order to focus a defined beam on the region of interest via the collimator settings. Individually controllable lead leaves, for example, can be provided as beam-limiting elements. The collimator is therefore disposed in the beam path from the X-ray generator 15 to X-ray detector 16 between the patient being examined and the X-ray generator 15. It is used to achieve sufficiently high image quality, e.g. by preventing blooming, and limiting the radiation dose to that necessary for the patient.

As has already been mentioned, the position data of the operator device 5, determined as described above, can be understood as operator position information, once the operator is holding the operator device 5 in his/her hand 17. However, it can also be used as the basis for deriving or estimating operator position information, particularly the operator's eyes. For example, a particular offset, a particular operator eye level and a particular viewing direction of the operator can be assumed.

In the example embodiment described here, however, the position data is used directly as operator position information in order to select, on the touchscreen 10 of the operator device 5, a perspective for a display used for adjusting the collimator settings and visualizing the X-ray beam in a three-dimensional manner. Preset perspectives in respect of a reference point of the medical technology device 1, in particular the center of the patient table 14 or the position of the patient table 14 which the central ray of the X-ray generator 15 would strike, are used. These perspectives may be defined, for example, by a ring of possible observation points. This then produces a perspective together with a viewing direction toward the reference point. The perspectives are selected such that an optimal, direction-dependent view of the X-ray beam (and in particular the patient table) is provided. To select a perspective, the observation point closest to the position described by the position information can be selected.

Figure 6:
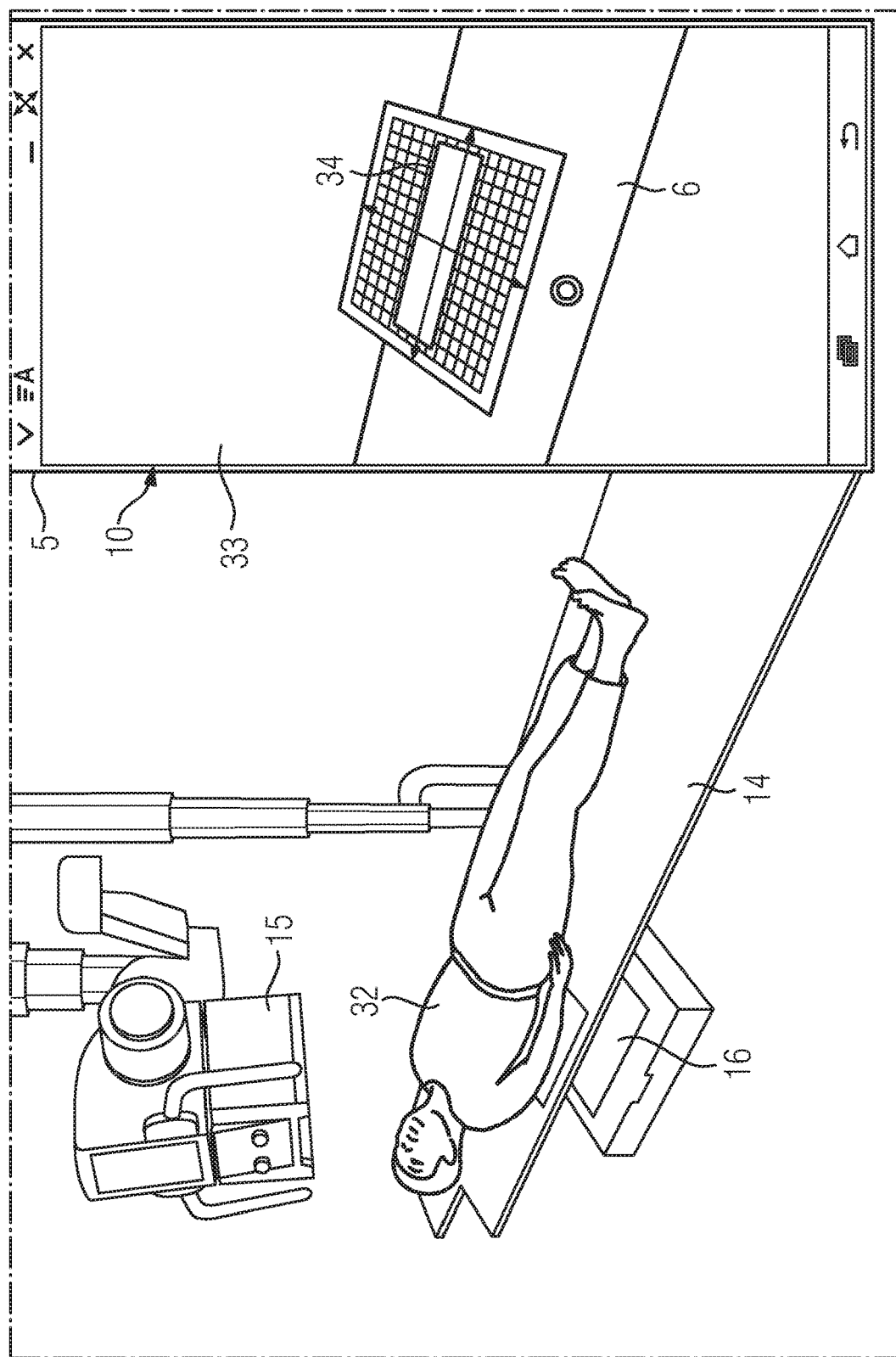
FIG. 6 shows the operator's perspective view of the medical technology device and a correspondingly generated display on the operator device for collimator setting.

FIG. 6 now shows side by side an operator view of the real medical technology device 1 comprising the patient table 14, the X-ray generator 15 with integral collimator and the X-ray detector 16, wherein a patient 32 to be examined has already been positioned on the patient table 14. Visible on the touchscreen display 10 of the operator device 5 is a display 33 derived from the position information and showing, from the selected perspective corresponding at least essentially to the operator's perspective of the real patient table 14, a virtual representation of the patient table 14 and, in the form of a rectangle 34, the resulting X-ray beam for the current collimator settings. By manipulating the rectangle 34 as a display element, the collimator settings can be changed, e.g. the beam can be reduced or enlarged by gripping the corners and/or displacement of the X-ray generator 15 and associated collimator can be achieved by displacing the entire rectangle 34. From the corresponding operator control information of the touchscreen 10, control information is derived which causes the collimator to be adjusted accordingly.

Returning to FIG. 3, if the patient 32 is positioned and the components 3 are set, it is then possible to proceed to a next step 35 of the medical technology workflow, cf. FIG. 3, in which an activation user interface is displayed on the touchscreen 10. The selected examination protocol 29 can then be started.

However, since in this case a radiation-using X-ray device is employed, it is first checked on the basis of the position data of the operator device 5 whether the operator is in a radiation-proof location, e.g. behind the radiation protection wall 22. Only then is it possible to trigger the examination process i.e. actually release the radiation. If the operator is in an unsafe location, the Operate control element can be grayed out and/or warning information issued.

When imaging is complete, an assessment user interface is displayed on the touchscreen 10 in which the X-ray image obtained as the examination result can undergo an initial assessment and, via corresponding operator control elements, first image processing algorithms can be used, annotations can be added (also by voice input) and/or a zoom function can be selected. For example, image sections of interest can be extracted (cropping), brightness and contrast can be adjusted, left/right marking and the like can be added. As the touchscreen 10 has a high-resolution display, sufficiently good assessment can be achieved; the touchscreen 23 can possibly be additionally used for the assessment.

The examination process can be terminated via another operator control element, wherein the examination result can then be sent e.g. to an information system/archiving system for archiving. It is then possible to proceed to the medical technology workflow of the next patient according to the list of patients, or the patient management user interface can be called up.

As indicated by the arrow 37, if a plurality of images of a patient 32 are to be prepared, the workflow steps 27, 30, 35 and 36 or, in the case of direct selection of a plurality of examination protocols, 30, 35 and 36, can then be repeated accordingly.

While it is basically conceivable, having regard to existing safety requirements, e.g. for triggering radiation, to provide a corresponding design of the operator device 5, it is also possible to use an expansion unit such as that described e.g. in the post-published patent applications DE 10 2017 217 128.6 and EP 17152779.9, the entire contents of each of which are hereby incorporated herein by reference.

Figure 7:
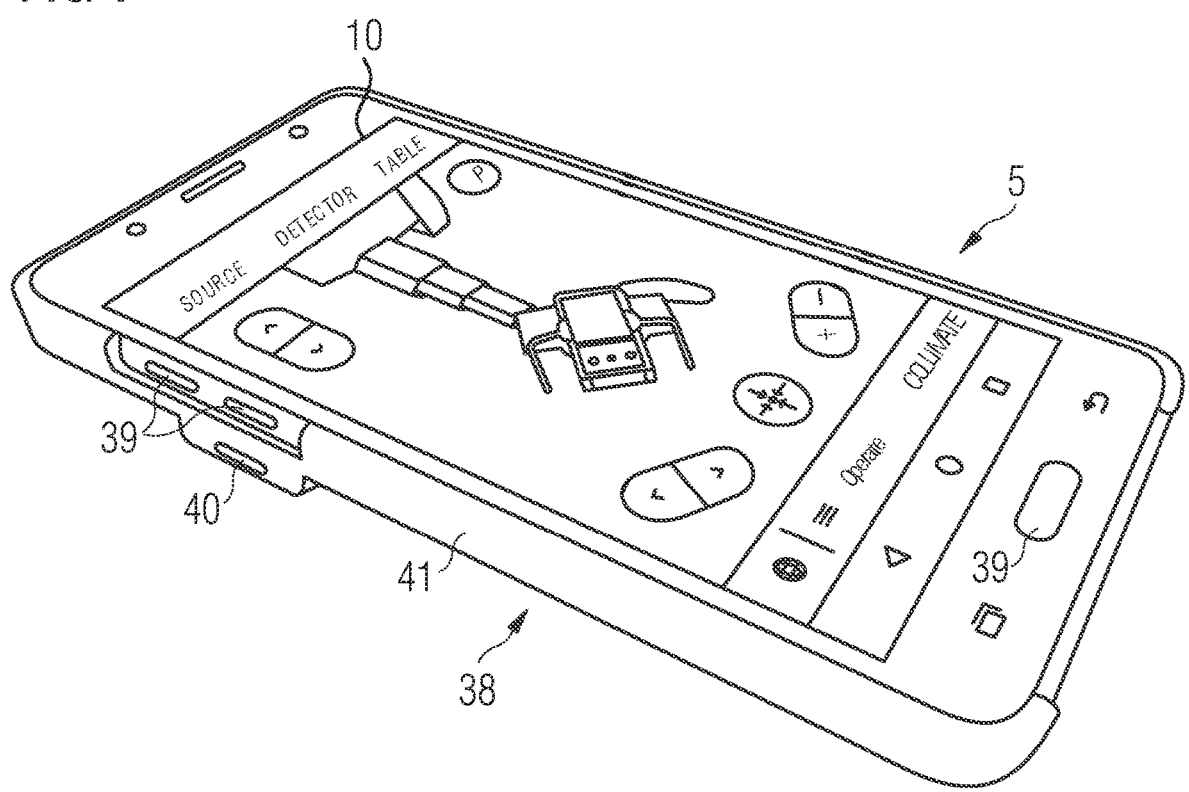
FIG. 7 shows a perspective view of the operator device with an expansion unit.

FIG. 7 shows an example of such an expansion unit 38 designed to meet the safety requirements and which is already connected to the operator device 5. It can be seen that the expansion unit 38 is implemented as a case 41 accommodating the operator device 5, wherein, in addition to operator control elements 39 of the operator device 5 that are provided next to the touchscreen 10, the expansion unit provides at least one other operator control element 40, here in the form of an enabling switch. Only when the enabling switch, i.e. the operator control element 40, is actuated is it possible for safety-critical control information to be implemented, e.g. moving of components 3 in the vicinity of the patient and the release of X-radiation. The expansion unit 38 can have communication interfaces for communicating with each of the control units 4, 6.

It is pointed out that the control units 4 and 6 can together usually constitute a control device which carries out the method according to the invention. However, embodiments are also conceivable in which at least the essential steps of the method according to the invention are carried out solely by the control unit 6 of the operator device 5. A corresponding control computer program can preferably be executed in a distributed manner or only on the control unit 6.

Finally, it should also be pointed out that a switching gesture by the operator on the touchscreen 10, in particular a swiping gesture, can be defined for switching between the different workflow-related user interfaces (steps 25, 27, 30, 35, 36).

Although the invention has been illustrated and described in detail by the preferred example embodiment, the invention is not limited to the examples disclosed and other variations will be apparent to persons skilled in the art without departing from the scope of protection sought for the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE CHARACTERS 1 medical technology device
2 room
3 component
4 control unit
5 operator device
6 control unit
7 communication link
8 short-range radio link
9 markers
10 touchscreen
11 operator device sensor
12 actuator
13 output device
14 patient table
15 X-ray generator
16 X-ray detector
17 hand
18 coverage area
19 camera
20 infrared LED
21 pointing direction
22 radiation protection wall
23 display device
24 carrying device
25 registration step
26 box
27 step
28 user interface
29 examination protocol
30 step
31 movement enabling button
32 patient
33 display
34 rectangle
35 step
36 step
37 arrow
38 expansion unit
39 operator control element
40 operator control element
41 expansion case
S1-S6 step

What is claimed is:

1. A method for controlling operation of a medical technology device using a wireless, hand-held, mobile operator device including a touchscreen, the method comprising: using the wireless, hand-held, mobile operator device for at least one of an examination and treatment procedure of at least one patient via the medical technology device, a medical technology workflow implemented via the wireless, hand-held, mobile operator device, for at least one of an examination and treatment procedure of the at least one patient via the medical technology device, comprising: acquiring patient data of the at least one patient from an acquisition user interface, selecting, via a selection user interface, a medical technology protocol containing operating parameters to be carried out for the at least one patient, tracking a position of the hand-held mobile operator device in the form of position data of the handheld mobile operator device the position data describing a position and orientation of the handheld mobile operator device relative to adjustable components of the medical technology device, wherein the position data is evaluated for selecting at least one of the adjustable components and ascertaining an operator input in respect of at least one of the components, setting remove-controllable adjustable components of the medical technology device, according to the at least one patient position in the medical technology device and according to the medical technology protocol, using a settings user interface, and activating, with the at least one patient positioned and components set, a medical technology procedure in an activation user interface.

2. The method of claim 1, wherein the patient data is acquired at least partially by at least one of:
   readout of an electronically readable code via a camera of the wireless, hand-held, mobile operator device; and
   readout of a radio-readable code via a radio readout interface of the wireless, hand-held, mobile operator device.

3. The method of claim 2, wherein the electronically readable code includes at least one of a barcode and a QR code, and wherein the radio-readable code includes at least one of an RFID tag and an NFC tag.

4. The method of claim 2, wherein, upon the at least one patient including a plurality of patients, the wireless, hand-held, mobile operator device includes, outside of the medical technology workflow for a current patient of the plurality of patients to be at least one of examined and treated, a patient management user interface via which a sequence of the plurality of patients to be at least one of examined and treated is adjusted according to a user input.

5. The method of claim 2, upon the at least one patient including a foreign-language patient, foreign-language information relating to a current position in the medical technology workflow is at least one of
   output to the foreign-language patient and
   words of the foreign-language patient, recorded using a microphone of the wireless, hand-held, mobile operator device, are translated into a language of the foreign-language patient and output by a translation program.

6. The method of claim 2, wherein, using the patient data, medical information describing an objective, of the at least one of examination and treatment, is determined, and wherein, depending upon at least one of medical technology protocols to be displayed, a sequence of the medical technology protocols and a medical technology protocol proposal are selected in the selection user interface.

7. The method of claim 2, wherein, for safety-relevant control commands, in addition to the wireless, hand-held, mobile operator device, an expansion unit is used, mechanically connectable or data-linkable to the wireless, hand-held, mobile operator device.

8. The method of claim 2, wherein, as another function of the medical technology workflow, in an examination process an initial output of an examination result takes place in an assessment user interface.

9. The method of claim 8, wherein the examination result includes an image, the assessment user interface provides at least one image processing option which, upon selection, applies, to the image, at least one of an image processing algorithm, a zoom function and an annotation function.

10. The method of claim 1, wherein, upon the at least one patient including a plurality of patients, the wireless, hand-held, mobile operator device includes, outside of the medical technology workflow for a current patient of the plurality of patients to be at least one of examined and treated, a patient management user interface via which a sequence of the plurality of patients to be at least one of examined and treated is adjusted according to a user input.

11. The method of claim 1, upon the at least one patient including a foreign-language patient, foreign-language information relating to a current position in the medical technology workflow is at least one of
output to the foreign-language patient and
words of the foreign-language patient, recorded using a microphone of the wireless, hand-held, mobile operator device, are translated into a language of the foreign-language patient and output by a translation program.

12. The method of claim 1, wherein, using the patient data, medical information describing an objective, of the at least one of examination and treatment, is determined, and wherein, depending upon at least one of medical technology protocols to be displayed, a sequence of the medical technology protocols and a medical technology protocol proposal are selected in the selection user interface.

13. The method of claim 1, wherein, for safety-relevant control commands, in addition to the wireless, hand-held, mobile operator device, an expansion unit is used, mechanically connectable or data-linkable to the wireless, hand-held, mobile operator device.

14. The method of claim 1, wherein, the wireless, hand-held, mobile operator device implemented includes at least one operator device sensor recording sensor data describing at least one of movement and position of the wireless, hand-held, mobile operator device in a room in which the medical technology device is located, and wherein position data, describing position and orientation of the wireless, hand-held, mobile operator device with respect to at least one of components to be set and movement data describing movement relative to the components, is determined from the sensor data and evaluated for at least one of selecting at least one of the components and determining an operator input in respect of at least one of the components.

15. The method of claim 1, wherein, as function of the medical technology workflow, in an examination process an initial output of an examination result takes place in an assessment user interface.

16. The method of claim 15, wherein the examination result includes an image, the assessment user interface provides at least one image processing option which, upon selection, applies, to the image, at least one of an image processing algorithm, a zoom function and an annotation function.

17. The method of claim 16, wherein the assessment user interface comprises a Finish operator control element which, when actuated, transfers a medical technology result to an archiving system.

18. The method of claim 15, wherein the assessment user interface comprises a Finish operator control element which, when actuated, transfers a medical technology result to an archiving system.

19. The method of claim 1, wherein the medical technology device is an imaging device, and wherein the wireless, hand-held, mobile operator device is a smart device.

20. The method of claim 1, further comprising determining a pointing direction of the hand-held, mobile operator device relative to the adjustable components of the medical technology device based on the position data.

21. A method for controlling operation of a medical technology device using a wireless hand-held mobile operator device including a touchscreen, the method comprising:
using the wireless, hand-held, mobile operator device for at least one of an examination and treatment procedure of at least one patient via the medical technology device, a medical technology workflow implemented via the wireless, hand-held, mobile operator device, for at least one of an examination and treatment procedure of the at least one patient via the medical technology device, comprising:
acquiring patient data of the at least one patient from an acquisition user interface,
selecting, via a selection user interface, a medical technology protocol containing operating parameters to be carried out for the at least one patient,
setting remote-controllably adjustable components of the medical technology device, according to the at least one patient positioned in the medical technology device and according to the medical technology protocol, using a settings user interface, and
activating, with the at least one patient positioned and components set, a medical technology procedure in an activation user interface
wherein, in an event of a user input indicating initiation of at least one of the examination and treatment procedure in a case of a radiation-using medical technology device, position of the wireless, hand-held, mobile operator device is determined and checked as to whether the wireless, hand-held, mobile operator device and the operator is in a radiation-protected location, and wherein initiation is only at least one of enabled and takes place upon a successful check.

22. A wireless, hand-held, mobile operator device for controlling the operation of a medical technology device, comprising:
a touchscreen; and
a control unit, designed to, for at least one of an examination and treatment procedure of at least one patient via the medical technology device, carryout a medical technology workflow for at least one of an examination and treatment procedure of the at least one patient via the medical technology device, the medical technology workflow including:
acquiring patient data of the at least one patient from an acquisition user interface,
selecting, via a selection user interface, a medical technology protocol containing operating parameters to be carried out for the at least one patient, tracking a position of the hand-held mobile operator device in the form of position data of the handheld mobile operator device the position data describing a position and orientation of the handheld mobile operator device relative to adjustable components of the medical technology device, wherein the position data is evaluated for selecting at least one of the adjustable components and ascertaining an operator input in respect of at least one of the components, setting remote-controllably adjustable components of the medical technology device, according to the at least one patient positioned in the medical technology device and according to the medical technology protocol, using a settings user interface, and activating, with the at least one patient positioned and components set, a medical technology procedure in an activation user interface.

23. A medical technology device, comprising the wireless, hand-held, mobile operator device of claim 22.

24. The medical technology device of claim 23, wherein the medical technology is an X-ray imaging device and comprises a radiation protection wall in a room.

25. An operating system for controlling the operation of a medical technology device, comprising:

a wireless, hand-held, mobile operator device including a touchscreen;

and a control device including a control unit of the wireless, hand-held, mobile operator device and a control unit of the medical technology device and designed to, for at least one of an examination and treatment procedure of at least one patient via the medical technology device, carry out a medical technology workflow for at least one of an examination and treatment procedure of the at least one patient via the medical technology device, the medical technology workflow including:

acquiring patient data of the at least one patient from an acquisition user interface, selecting, via a selection user interface, a medical technology protocol containing operating parameters to be carried out for the at least one patient, tracking a position of the hand-held mobile operator device in the form of position data of the handheld mobile operator device the position data describing a position and orientation of the handheld mobile operator device relative to adjustable components of the medical technology device, wherein the position data is evaluated for selecting at least one of the adjustable components and ascertaining an operator input in respect of at least one of the components, setting remove-controllable adjustable components of the medical technology device, according to the at least one patient positioned in the medical technology device and according to the medical technology protocol, using a settings user interface, and activating, with the at least one patient positioned and components set, a medical technology procedure in an activation user interface.

26. A medical technology device, comprising the operating system of claim 25.

27. The medical technology device of claim 26, the medical technology device being implemented as an X-ray imaging device and comprising a radiation protection wall in a room.

* * * * *